(12) United States Patent
Jones et al.

(10) Patent No.: US 11,291,610 B2
(45) Date of Patent: Apr. 5, 2022

(54) HARVESTING ENERGY DURING COMPRESSION OF A PILL PACK

(71) Applicant: KONINKLIJKE PHILIPS N.V., Eindhoven (NL)

(72) Inventors: Adam Jones, Eindhoven (NL); Kiran Hamilton J. Dellimore, Utrecht (NL); Martin Grüterich, Aachen (DE); Arthur Bouwman, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 127 days.

(21) Appl. No.: 16/621,722

(22) PCT Filed: Jun. 13, 2018

(86) PCT No.: PCT/EP2018/065582
§ 371 (c)(1),
(2) Date: Dec. 12, 2019

(87) PCT Pub. No.: WO2018/229091
PCT Pub. Date: Dec. 20, 2018

(65) Prior Publication Data
US 2021/0137792 A1   May 13, 2021

(30) Foreign Application Priority Data
Jun. 16, 2017 (EP) .................................... 17176328

(51) Int. Cl.
*A61J 1/03* (2006.01)
*A61J 7/00* (2006.01)
*G16H 40/67* (2018.01)

(52) U.S. Cl.
CPC ............. *A61J 7/0076* (2013.01); *A61J 1/035* (2013.01); *G16H 40/67* (2018.01); *A61J 2200/30* (2013.01)

(58) Field of Classification Search
CPC ................................ A61J 7/0076; A61J 1/035
See application file for complete search history.

(56) References Cited

U.S. PATENT DOCUMENTS

| | | | |
|---|---|---|---|
| 5,412,372 A | 5/1995 | Parkhurst et al. | |
| 7,884,727 B2 * | 2/2011 | Tran | A61B 5/7275 340/573.1 |

(Continued)

FOREIGN PATENT DOCUMENTS

| | | |
|---|---|---|
| ES | 2404138 B1 | 8/2014 |
| WO | 1996004881 A1 | 2/1996 |

(Continued)

OTHER PUBLICATIONS

International Search Report and Written Opinion, International Application No. PCT/EP2018/065582, dated Aug. 6, 2018.
Haynes, R. et al., "Interventions for enhancing medication adherence", Cochrane Systematic Review—Intervention Version published: Apr. 16, 2008.
Brown, M. et al., "Medication Adherence: WHO Cares?", Mayo Clin Proc. Apr. 2011; 86(4): 304-314NPL.

(Continued)

*Primary Examiner* — Gene O Crawford
*Assistant Examiner* — Ayodeji T Ojofeitimi (57) ABSTRACT

Various methods and apparatus disclosed herein relate to apparatus and techniques for harvesting energy from operation of a pill pack, and utilizing that energy for various purposes. In various embodiments, an energy harvesting apparatus configured to receive a pill pack (104, 304) is disclosed. An energy harvesting apparatus in accordance with various embodiment may include a housing (102, 302), where the housing is configured to receive a pill pack (104, 304), and an electrical generator incorporated into the housing (102, 302), where the electrical generator converts motion associated with compression of at least one blister ($103_{1-n}$, $303_{1-n}$) of the pill pack (104, 304) expelling one or more pills ($105_{1-n}$, $305_{1-n}$) from the pill pack into electrical energy, where the electrical energy is used to collect one or (Continued)

more data points associated with operation of the pill pack during the expelling of the one or more pills.

13 Claims, 4 Drawing Sheets

(56) References Cited

U.S. PATENT DOCUMENTS

| | | | |
|---|---|---|---|
| 2013/0087469 A1 | 4/2013 | Khasnis | |
| 2013/0201316 A1* | 8/2013 | Binder | H04L 67/12 348/77 |
| 2015/0347713 A1 | 12/2015 | Seeger | |
| 2016/0132661 A1 | 5/2016 | Dixit et al. | |

FOREIGN PATENT DOCUMENTS

| | | |
|---|---|---|
| WO | 2003090663 A1 | 11/2003 |
| WO | 2008000479 A1 | 1/2008 |

OTHER PUBLICATIONS

"Medication Adherence—Taking Your Meds as Directed", https://www.heart.org/en/health-topics/consumer-healthcare/medication-information/medication-adherence-taking-your-meds-as-directed#.V1kvmJjVyM8, Accessed Dec. 9, 2019.

"MEMS Adherence Hardware", https://www.aardexgroup.com/solutions/mems-adherence-hardware, Accessed Dec. 9, 2019.

"AdhereTech", https://www.adheretech.com/, Accessed Dec. 9, 2019.

"Products and Devices to Help You Identify Your Medications", VisionAware, 2019 American Printing House for the Blind, https://www.visionaware.org/info/essential-skills-2/managing-your-medication/products-and-devices-to-help-you-identify-your-medications/235.

"Push-Out Test for Pills in Push-Through-Packs", Shimadzu, 2019 Shimadzu Corporation, https://www.shimadzu.com/an/industry/pharmaceuticallifescience/n9j25k00000dpjsa.html.

Mannion, P., "Comparing Low-Power Wireless Technologies", Digi-Key, Oct. 2017.

* cited by examiner

HARVESTING ENERGY DURING COMPRESSION OF A PILL PACK

CROSS-REFERENCE TO PRIOR APPLICATIONS

This application is the U.S. National Phase application under 35 U.S.C. § 371 of International Application No. PCT/EP2018/065582, filed on 13 Jun. 2018, which claims the benefit of European Patent Application No. 17176328.7, filed on 16 Jun. 2017. These applications are hereby incorporated by reference herein.

TECHNICAL FIELD

The present invention is directed generally to health care. More particularly, various methods and apparatus disclosed herein relate to apparatus and techniques for harvesting energy from the expulsion of one or more pills from a pill pack and utilizing that energy for various purposes.

BACKGROUND

Compliance with prescribed medication regimens is a problem among patients of all ages and backgrounds. The causes of non-compliance are complex and multi-factorial. Some of the principal factors that have been identified as potentially contributing to non-compliance include: 1) the economic burden related to a patient's disease or comorbid conditions; 2) poor patient-caregiver/healthcare provider relations; 3) perceived stereotypes and misconceptions related to a patient's condition; 4) a patient's lack of involvement in the decision-making process; 5) medication errors (linked to incorrect identification of medication); and, 6) improper or incorrect medication administration (e.g. taking the wrong medication or under or over dosing of medication).

Conventional products exist that partially address some of the factors that underlie non-compliance with medication regimens. These include pill containers, customized pill packaging, smartphone applications, audible medication identification devices (for preventing medication errors due to incorrect identification), and the like. However, these products suffer from a variety of shortcomings, for example they do not address the multiple and co-existing factors contributing to poor medication adherence. Additionally, conventional products do not harvest energy expended during compression of a pill pack, e.g., to power data transmission to one or more remote computing devices and/or to automatically log information regarding compliance in a patient's medical record.

WO03090663 A1 discloses a content use monitoring system for monitoring use of blister packaged contents.

SUMMARY

The present disclosure is directed to methods and apparatus for harvesting energy from the operation of the pill pack, including the compression of at least one blister of a pill pack. Generally, in one aspect, an energy harvesting apparatus configured to receive a pill pack according to various embodiments described herein contains a housing, where the housing is configured to receive a pill pack, and an electrical generator incorporated into the housing, where the electrical generator converts motion associated with compression of at least one blister of the pill pack expelling one or more pills from the pill pack into electrical energy. The electrical energy is used to collect one or more data points associated with operation of the pill pack during the expelling of the one or more pills.

In some embodiments, the one or more data points associated with the operation of the pill pack includes an identification of the one or more pills expelled from the pill pack. In some embodiments, the energy harvesting apparatus further comprises an identification button, where the identification button is positioned so as to be activated when the one or more pills are expelled from the pill pack. In other embodiments, the identification of the one or more pills expelled from the pill pack is determined based on a level of force required to expel the one or more pills.

In some embodiments, the energy-harvesting apparatus further comprises a low power wireless transmitter integral with the housing, where at least some of the electrical energy is used to wirelessly transmit, from the low power wireless transmitter to a remote computing device one or more of data points. In other embodiments, the low power wireless transmitter is a Bluetooth low energy transmitter, a ZigBee transceiver, or an EnOcean transceiver. In still other embodiments, the one or more data points associated with the operation of the pill pack collected, include a timestamp.

In other aspects, a method for harvesting and using electrical energy during compression of a pill pack is disclosed. Such a method comprises inserting the pill pack into a housing configured to receive the pill pack; operating the pill pack, where operating includes compressing at least one blister of the pill pack to expel at least one pill from the pill pack; converting, by an electrical generator that is integral with the housing, motion associated with compression of the at least one blister into electrical energy; and, using at least some of the electrical energy to at least temporarily store, in a memory component integral with the housing, one or more data points associated with operation of the pill pack.

In some embodiments, operating the pill pack further comprises identifying the one or more pills expelled from the pill pack. In other embodiments, the one or more data points include an identification of the at least one pill expelled from the pill pack.

In some embodiments, the electrical generator comprises a linear alternator. In other embodiments, the electrical generator comprises a piezoelectric strip.

In some embodiments, the method further comprises utilizing at least some of the electrical energy to wirelessly transmit, from a low power wireless transmitter integral with the housing to a remote computing device, one or more of the data points. In some embodiments, the low power wireless transmitter is a Bluetooth low energy transceiver or a ZigBee transceiver. In other embodiments, the one or more data points include a timestamp indicating a time the at least one pill was expelled from the pill pack.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

Conventional products for addressing non-compliance with medication regimens suffer from a variety of shortcomings. These products may not address the multiple and co-existing factors contributing to poor medication adherence. Additionally, conventional products may not provide a method(s) for harvesting energy expended during compression of a pill pack to power data storage and/or transmission. In view of the foregoing, various embodiments and implementations of the present disclosure are directed to harvesting energy from the operation of a pill pack in a housing, and utilizing that energy for various purposes.

Figure 1:
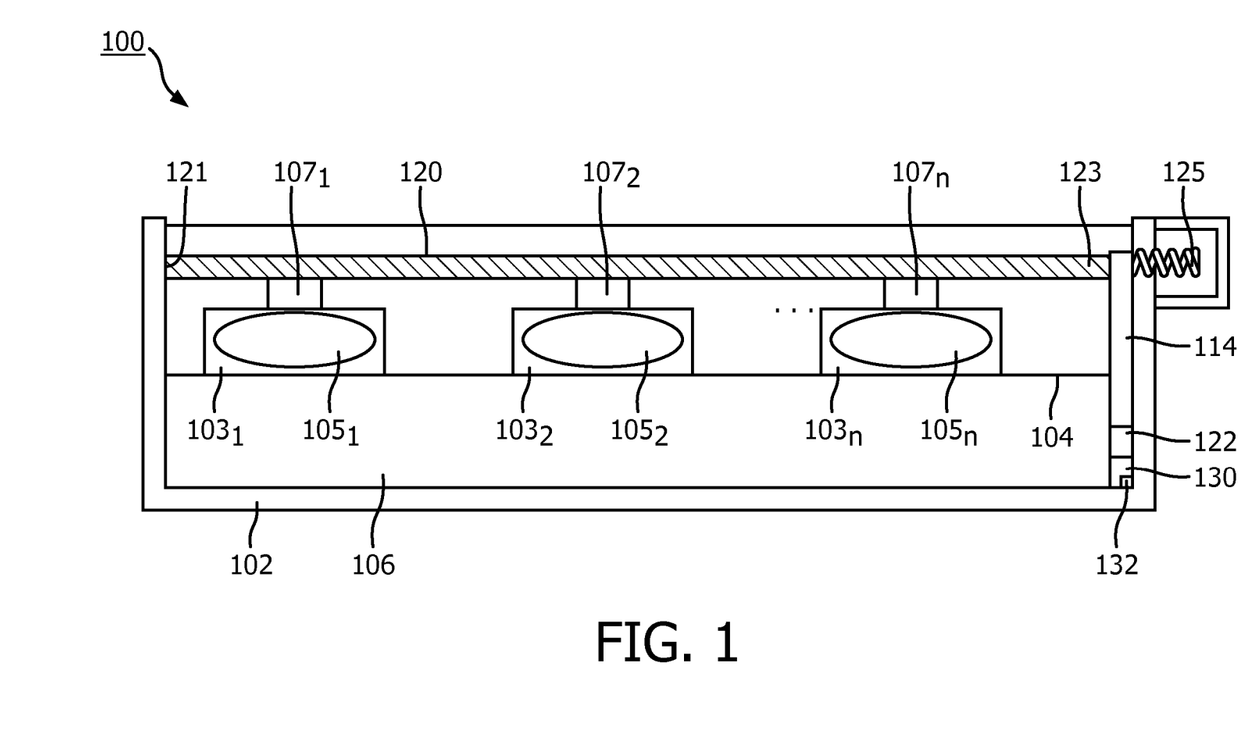
FIG. 1 illustrates a cross-sectional view of an example energy harvesting apparatus capable of receiving a pill pack and configured with selected aspects of the disclosure, in accordance with various embodiments.
Figure 2:
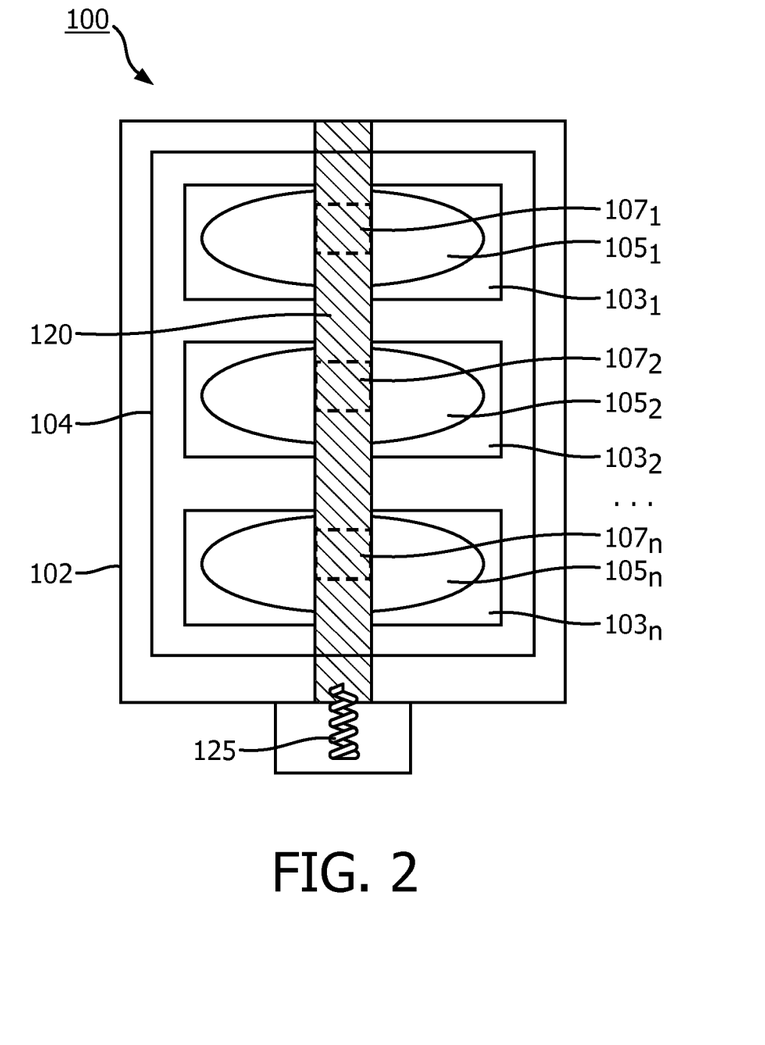
FIG. 2 illustrates a top view of the example energy harvesting apparatus of FIG. 1 with selected aspects of the present disclosure, in accordance with various embodiments.

FIGS. 1 and 2 illustrate an example energy-harvesting apparatus 100 configured with selected aspects of the present disclosure depicted in cross section (FIG. 1) and in top view (FIG. 2). The energy harvesting apparatus 100 may include a housing 102. In some embodiments, the housing 102 may be in the form of a sleeve or box that removably receives a pill pack, for example a pill pack may slide into the housing 102. In other embodiments the housing 102 may permanently receive a pill pack and may not be reusable. In still other embodiments the housing 102 may also serve to hold a pill pack into a desired position.

A pill pack used in conjunction with the housing 102 may contain any number of pills deemed necessary by a medical professional for a course of treatment. In some embodiments, this may be one month's supply, while in other in embodiments this may be one week's supply, and so forth. A pill pack used in conjunction with an energy harvesting apparatus may have one or more blister compartments (referenced herein as "blisters"), each containing one or more pills. The blisters may be divided by the day and time of administration of the one or more pills, so that all pills required to be taken at each time throughout the week are stored within the same compartment. Generally, these blisters are created with a covering (usually in the form of a bubble) over the selected pill(s) that is attached to a backing. In some embodiments the blister covering may be a plastic material of varying thickness. In other embodiments, a single piece of plastic may be used as a cover for the entire pill pack, with individual blisters created therefrom. In some embodiments, the backing may be aluminum foil of varying thickness. Although FIGS. 1 and 2 illustrate a linear arrangement of blister compartments and associated pills, this is not intended to be limiting. A pill pack may include one or more blisters arranged linearly or in a grid, for example a 4×7 grid may be used to dispense four weeks or 28 days of medication. FIGS. 1 and 2 illustrate a pill pack 104 and associated blister compartments $103_{1-n}$ within the housing 102. The housing 102 may include an interior area 106, which may receive one or more pills after being expelled from a blister.

As noted above, embodiments described herein are generally directed to harvesting energy during operation of a pill pack and utilizing the harvested energy for various purposes. Accordingly, an energy harvesting apparatus 100 may include a variety of integral components that facilitate conversion of motion associated with expelling one or more pills $105_{1-n}$ from blisters $103_{1-n}$ of pill pack 104 into electrical energy. The example depicted in FIG. 1, for instance, may include a linear alternator 114. In some embodiments, the linear alternator 114 may include one or more conductive coils and a ferromagnetic element (not illustrated in FIG. 1 or 2). The ferromagnetic element may be moved inside the conductive coil via one or more bands 120 positioned over the pills $105_{1-n}$.

The one or more bands 120 positioned over the pills $105_{1-n}$ may be under tension. In some embodiments a single band may run the length of a row or column of pills, where the pill pack is a grid or array. In some embodiments, these bands may be made of a stiff polymer; in other embodiments, these bands may be made of a rubber-band-like material. A first end 121 of the band 120 may be securely fixed to the housing 102, while a second end 123 of the band 120 may be connected to the ferromagnetic element of the linear alternator 114 and a spring 125. Consequently, any vertical movement of the one or more bands 120 during the compression of a blister to expel one or more pills may cause the ferromagnetic element to be displaced within the conductive coil. However, this is not to be understood as limiting; any trigger mechanism for the movement of the ferromagnetic element known in the art may be used for example, a vertically-moving stage located directly above the alternator may trigger the desired movement.

As an illustrative example, when a user desires a pill 105 from the pill pack 104, the user may apply pressure to (i.e. press down in FIG. 1) on the band 120 above the blister 103 containing the desired pill 105 in order to push down on the pill(s) to break them free of the packaging. Pushing down on a band 120 may pull the spring 125 inward (to the left in FIG. 1), which may prevent excess force from being applied to neighboring blisters 103 and minimize the risk of inadvertently dispensing an additional pill(s) from a neighboring blister. Energy may therefore be harvested (according to Faraday's law of induction), as the band 120 stretches (or a similar component moves) downwards towards the blister until the pill 105 has been pushed free of the packaging. According to Faraday's Law, the movement of the ferromagnetic element relative to conductive coils may induce a current in conductive coils, and the flow of electrons forming this current may, for instance, charge a capacitor with electrical energy, which may then be used for a variety of purposes.

Energy harvested may be temporarily stored in a capacitor 122 or super-capacitor as it is generated until the end of motion and expulsion of the one or more pills from the blister of the pill pack. At the conclusion of the motion, and expulsion of the one or more pills, the harvested energy may be discharged automatically, e.g., to send a low-power data transmission to a remote computing device (e.g., smartphone, smart watch or tablet, network, computer, or the like) operated by a user (e.g., a patient and/or medical personnel), denoting that one or more pills have been successfully removed from the packaging.

In some embodiments, the apparatus 100 may include onboard circuitry 130, which may include a transmitter 132 (or in some cases a transceiver). A transmitter 132 may be configured to communicate wirelessly with one or more remote computing devices (not depicted in FIG. 1 or 2) using various low energy wireless technologies, such as Bluetooth low energy (e.g., Bluetooth 4.0), ANT, ANT+, infrared data association ("IrDA"), ZigBee, Z-Wave, low power Wi-Fi, near field communication ("NFC"), EnOcean radiofrequency transmission protocol, and so forth. In some embodiments, electrical energy harvested during compression of the one or more blisters $103_{1-n}$ and expulsion of the one or more pills $105_{1-n}$ from the pill pack 104 into interior 106 of the housing may be used to power wireless transmission of data to one or more remote computing devices. In some embodiments, the remote computing device may store data point(s), e.g., in association with a timestamp generated by the remote computing device.

Expelling one or more pills $105_{1-n}$ from (individual blisters $103_{1-n}$) of a pill pack 104 may generate one or more data points associated with the operation of the operation of the pill pack. In some embodiments, these data points may include an identification of which pill(s) were expelled from the pill pack. This information may be useful for a caregiver or medial provider so that they may track which particular pills were or were not (presumably) taken by a patient. In some embodiments, the identification of an expelled pill(s) may be used in conjunction with an alert system to determine whether the correct medication is being administered at the correct time. With such an alert system, steps may be taken to warn a user of poor adherence, or to assist in the prevention of an incorrect administration of medication by alerting a patient that the incorrect pill(s) was expelled prior to the patient swallowing the pill(s).

In some embodiments, an identification button 107 is located on top of a blister compartment 103 and below the band 120. This button 107, where present, may be pressed or otherwise actuated during the compression of the blister 103 in order to expel the pill(s) and may be used to identify which pill(s) a user has been dispensed (and presumably taken). In some embodiments, the identification buttons 107 may be coupled together via a circuit, such that actuation of any given identification button 107 may cause output in the form of a unique identification number to be provided. In other embodiments, a predetermined level of force may be required in order to trigger the identification button 107. Such a predetermined force requirement may be particularly useful when in preventing the inadvertent triggering of an identification button due to accidental contact with the apparatus, such as during travel. In some embodiments, a remote computing device may compare the data generated from pressing the identification button 107 with previously received data to determine whether the compression was over a valid blister compartment (i.e., a compartment containing one or more pills), or one that is invalid (i.e., has been emptied previously without a refill or which is not the correct pill to be taken). In still other embodiments, once the identification buttons 107 for all pills in the pill pack are known to have been pressed, a remote computing device may send a pill pack refill alert to a user, caregiver, medical professional (e.g. physician, pharmacy, etc.) indicating it may be time to refill the prescription. In some embodiments, the energy harvesting apparatus 100 may be reused once the empty pill pack has been removed, and a new pill pack may be loaded/inserted into the energy harvesting apparatus.

In other embodiments, the identification of which pill(s) were expelled from the pill pack may be determined by comparing a measurement of the force required to expel a pill(s) from a particular blister compartment with a known standard and/or with other blister compartments. In such an embodiment, a pill pack utilized may have varying degrees of force required to expel a pill(s) from a blister compartment depending on the placement of the blister compartment. For example, a blister compartment in the upper right quadrant of a pill pack with a 2-by-2 grid may require more force to expel the pill(s) contained therein than the blister compartment of the lower left quadrant of the same pill pack. This difference may be used to identify which pill(s) were expelled without the use of an identification button 107.

In some embodiments, onboard circuitry 130 may further include some form of rudimentary memory (not illustrated in FIG. 1 or 2) coupled to the transmitter or transceiver for storing one or more data points associated with operation of the energy-harvesting apparatus 100. For example, in some embodiments, an identification of which pill(s) have been expelled may be stored at least temporarily in a memory component. The memory component may take various forms that may or may not be considered "low power" because only a minimal amount of electrical energy is required to read from, and/or write to the memory component. In some embodiments, memory component may be non-volatile, and may include one or more of the following: random access memory ("RAM"), programmable ready-only memory ("PROM"), erasable PROM ("EPROM"), electrically erasable PROM ("EEPROM"), flash memory (NAND or NOR), Ferroelectric RAM ("FeRAM"), Programmable metallization cell ("CBRAM"), parallel random-access machine ("PRAM"), Silicon-Oxide-Nitride-Oxide-Silicon ("SONOS"), Resistive random-access memory ("RRAM"), racetrack memory, Nano-RAM, and so forth.

In order to determine the amount of energy capable of being harvested, assume that when a user presses on a blister $103_{1-n}$ of a pill pack to expel one or more pills $105_{1-n}$ from a blister $103_{1-n}$ from a pill pack 104, a force F of 30-40 N is applied. Application of such a force F over a distance D of 5-10 mm during operation of a pill pack 104 may yield the following equation to calculate (gross) harvested energy $E_{gross}$:

$$E_{gross} = F \times D = (30\text{-}40 \text{ N}) \ast (0.050\text{-}0.010 \text{ m}) = 0.150\text{-}0.400 \text{ J} \quad (1)$$

Even accounting for 40% energy loss, the net energy harvested $E_{net}$ may be estimated as follows:

$$E_{net} = 0.6 \ast E_{gross} = 0.6 \ast (0.150\text{-}0.400) = 0.090\text{-}240 \text{ J} \quad (2)$$

In some embodiments, the maximum force required to remove a pill from a blister of a pill pack may vary with packaging design. Where the backing of a pill pack is aluminum foil, a peak force needed to rupture the aluminum foil may be approximately 15 N. However, the force required to push a pill completely free of the packaging may depend on the thickness and stiffness of the plastic blister of the pill pack. Therefore, the amount of energy capable of being harvested may vary between differing types of pill packs.

A simple energy budget calculation may be used to confirm that the net energy generated $E_{net}$ is sufficient to transmit one or more data points using transmitter 132 is harvested:

$$E_{net} = E_{gross} - (E_{xmit} + E_{loss}) \quad (3)$$

$E_{xmit}$ represents energy required to transmit one or more data points. $E_{loss}$ represents energy losses, which assuming 40% energy losses, may be calculated as $0.4 \times E_{gross}$.

Suppose that ZigBee or low-power Wi-Fi is employed for wireless transmission, and that estimated energy losses are 40%. In some embodiments, 0.036 J of electrical energy $E_{xmit}$ may be consumed during data transmission. The power requirement for low-power Wi-Fi/ZigBee is 36 mJ per 24 bytes of data, for Bluetooth low energy it is less, 0.147 mJ, and for EnOcean radiofrequency even less, as little as 100-200 µJ. Suppose $E_{gross}$ is 0.150 J, which means $E_{loss}$ is 0.060 J. Plugging the values set forth above into Equation (3) shows that there is sufficient net energy $E_{net}$ to acquire, store, and transmit data:

$$0.054 = 0.150 \text{ J} - (0.036 \text{ J} + 0.036 \text{ J} + 0.060 \text{ J}) = 0.054 \text{ J} \quad (4)$$

The equations above are examples only, and are not meant to be limiting. Even more energy may be generated if compression force required to expel one or more pills $105_{1-n}$ from a pill pack 104 is greater.

In some embodiments, apparatus 100 may include (e.g., coupled with onboard circuitry 130) one or more output devices, such as one or more light-emitting diodes ("LEDs") (not illustrated in FIGS. 1 and 2). These output components, where present, may be located at various positions on apparatus 100, such as on a portion of housing 102. In some such embodiments, one or more LEDs may be illuminated (e.g., with a green color), for instance, when a successful data transmission has taken place. In other embodiments, one or more LEDs may be illuminated (e.g. with a red color) for instance, when there has been insufficient power harvested to allow for data transmission, indicating to a user the need to apply additional compressive force to the particular blister compartment in order to allow data transmission to occur. In some embodiments, the output devices, such as one or more LEDs may be wirelessly coupled with a remote computing device and may serve as a notification system that the removal/expulsion of a pill(s) was successfully logged. For example, one more LEDs may illuminate green to signal to a user that data was successfully transmitted to a remote computing device.

Figure 3:
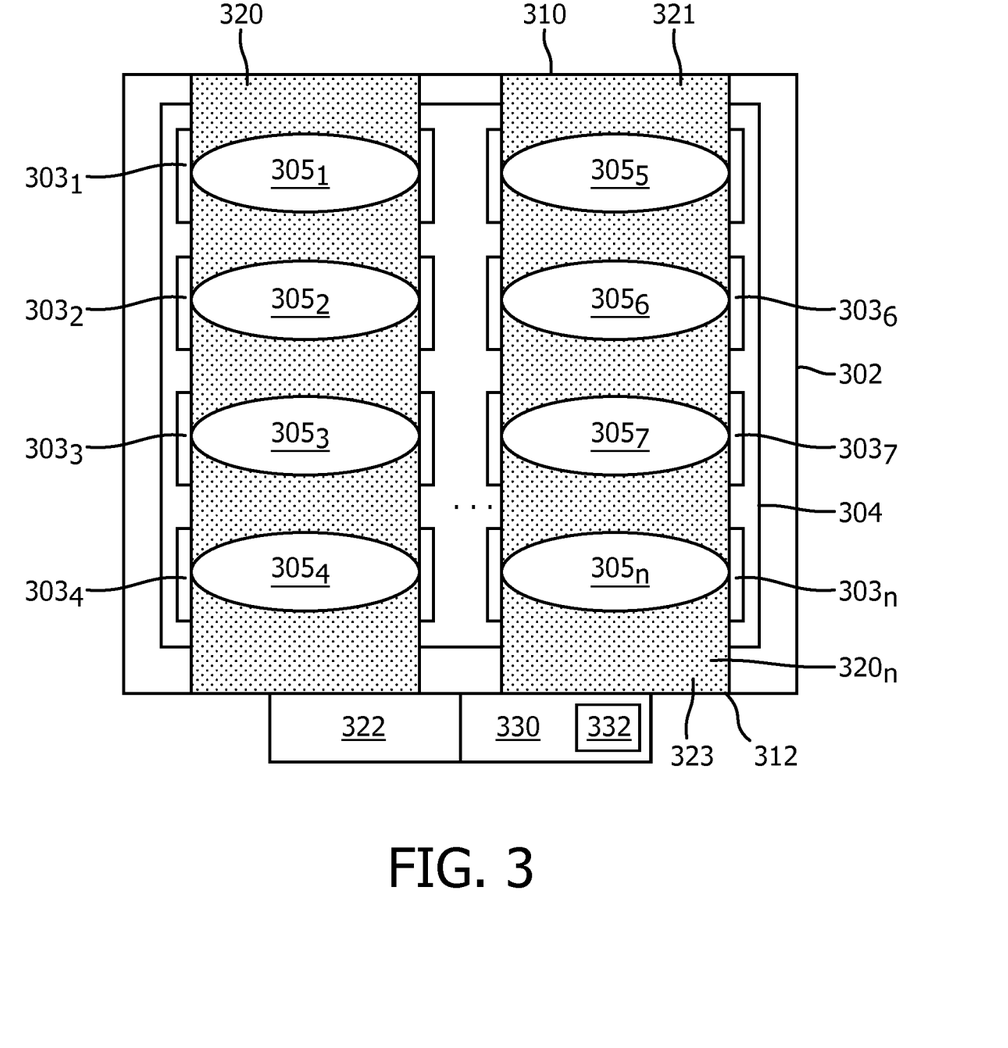
FIG. 3 illustrates a top view of another example energy harvesting apparatus capable of receiving a pill pack and configured with selected aspects of the disclosure, in accordance with various embodiments.

FIG. 3 illustrates another example energy-harvesting apparatus 300 configured with selected aspects of the present disclosure depicted in top view. As illustrated in FIG. 3, the energy harvesting apparatus 300 may include a housing 302. Similar to the embodiments described previously in conjunction with FIGS. 1 and 2, the housing 302 may be in the form of a sleeve or box that removably receives a pill pack. For example, a pill pack may slide into the housing 302 and may hold the pill pack in a desired position. In other embodiments the housing may permanently receive a pill pack and may not be reusable. A pill pack 304 used in conjunction with the housing 302 may be similar to the pill packs described in conjunction with FIGS. 1 and 2, and may have one or more blister compartments $303_{1-n}$ each containing one or more pills $305_{1-n}$. As described previously, the blisters 303 may be divided by the day and time of administration of the pill(s) therein. Generally, these blisters 303 are created by a covering (usually in the form of a bubble) over the selected pill(s) attached to a backing. In some embodiments the blister covering may be a plastic material of varying thickness. In other embodiments, a single piece of plastic may be used as a cover for the entire pill pack, with individual blisters created therein. In some embodiments, the backing may be aluminum foil of varying thickness. The pill pack 304 comprises one or more blisters 303, which may be arranged linearly or in a grid or array. FIG. 3 illustrates a pill pack 304 and associated blister compartments $303_{1-n}$ within a housing 302.

As discussed previously, embodiments described herein are generally directed to harvesting energy during operation of a pill pack and utilizing the harvested energy from the conversion of motion associated with expelling one or more pills $305_{1-n}$ from (individual blisters $303_{1-n}$) of a pill pack 304 into electrical energy various purposes. In the example embodiment depicted in FIG. 3, for instance, one or more strips $320_{1-n}$ of piezoelectric material may be arranged above the pill(s) $305_{1-n}$ as they are stored in blister compartments $303_{1-n}$. In some embodiments, the piezoelectric material may be lead zirconate titanate (PZT). In other embodiments, the piezoelectric material used may be aluminum nitride, barium titanate, potassium sodium niobate (KNN), and/or bi-layered bismuth sodium titanate (BNT), all which may have the advantage of being lead-free. A first end 321 of a piezoelectric strip 320 is attached to and supported by a first end 310 of the housing 302, while a second end 323 of a piezoelectric strip 320 is attached and supported at a second end 312 of the housing 302, where the first and second ends, 314, 312 of the housing 302 oppose each other.

As a user compresses a blister compartment $303_{1-n}$ downward (i.e. into the page in FIG. 3) to expel the pill(s) $305_{1-n}$ contained therein, the action may push a piezoelectric strip 320 downward onto pill(s) 305 below. Once the downwards force is released, typically once the pill(s) has been expelled, piezoelectric strip 320 may snap back into its original position. The strain applied to the piezoelectric strip 320 generates an alternating current, and provides a way to harvest energy on an event basis from the operation of the pill pack 304. In some embodiments, a bridge rectifier may also be utilized to convert the AC current into DC current, which may in turn charge a capacitor or super-capacitor, and energy harvested may be temporarily stored in a capacitor 322 or super-capacitor as it is generated until the end of motion and expulsion of the one or more pills from the blister of the pill pack.

In some embodiments, the apparatus 300 may include onboard circuitry 330, which may include a transmitter 332 (or in some cases a transceiver). A transmitter 332 may be configured to communicate wirelessly with one or more remote computing devices (not depicted in FIG. 3) using various low energy wireless technologies, such as those mentioned above. In some embodiments, electrical energy harvested during compression of the one or more blisters $303_{1-n}$ and expulsion of the one or more pills $305_{1-n}$ from the pill pack 304 may be used to power wireless transmission of data to one or more remote computing devices. In some embodiments, the remote computing device may store data point(s), e.g., in association with a timestamp generated by the remote computing device.

In general, automatically harvesting energy as described herein and using that energy to store information about pill identification, pill characteristics (e.g. dosage), time expelled from blister of pill pack (and presumably taken), and/or to make that information available on one or more remote computing devices, may have a number of technical advantages. Some such technical advantages of the various embodiments disclosed herein may include, but are not limited to, lessening the burden on patients to log their medication intake, reliability of tracking as an energy-harvesting apparatus, such as described herein, does not require batteries that may need replacing, etc. Therefore, medical personnel, caregivers, and the like may be able to more accurately monitor compliance with medication regimes. This may in turn reduce errors that might otherwise result from distractions, etc. Data collected may be used to update the patient's medical record, to trigger reminders to the patient in cases of partial or non-compliance in medication regime, and the like.

Figure 4:
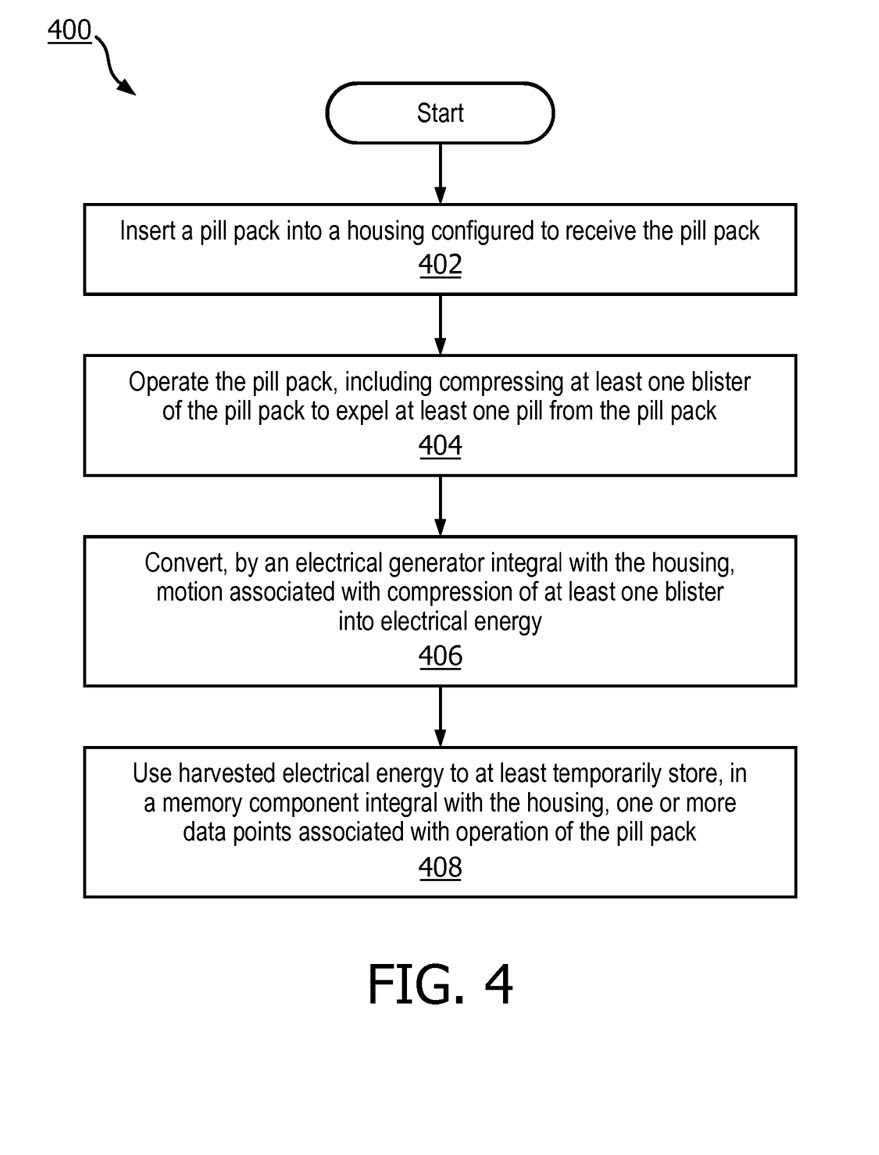
FIG. 4 depicts an example method of performing various techniques described herein, in accordance with various embodiments.

FIG. 4 depicts an example method 400 of performing various techniques described herein, in accordance with various embodiments. Although particular operations of method 400 are shown in a particular order, this is not meant to be limiting. In various embodiments, one or more operations may be added, omitted, and/or reordered.

At block 402, a pill pack (e.g. 104, 304) is inserted into a housing (e.g. 102, 302) configured with selected aspects of the present disclosure. In some embodiments, the housing may be in the form of a sleeve or box that removably receives a pill pack (e.g. 104, 304), for example a pill pack may slide into the housing. In other embodiments the housing may permanently receive a pill pack and may not be reusable. In still other embodiments the housing may also serve to hold a pill pack into a desired position.

At block 404, a pill pack received by the housing is operated, which may include compressing at least one blister (e.g. $103_{1-n}$, $303_{1-n}$) of the pill pack in order to expel at least one pill (e.g. $105_{1-n}$, $305_{1-n}$) from the pill pack. These blisters may be divided by their day and time of administration, so that all pills required to be taken at each time throughout the day, week, etc. are stored within the same compartment. Operating the pill pack to expel one or more pills may involve pressing down on one or more blisters such that the one or more pills break through the (e.g., aluminum) backing and can be pushed through; the force required to compress the blister and expel the pill(s) may also vary.

At block 406 motion associated with the compression of one or more blisters may be converted into electrical energy. In some embodiments, a linear alternator may be used for the generation of electrical energy. In other embodiments, a piezoelectric strip may be used to generate electrical energy.

At block 408, at least some of the electrical energy harvested during operation of the pill pack may be used to at least temporarily store one or more data points in a memory component integral with the housing. These data points may include, but are not limited to, the identification of the pill(s) expelled, the dosage of the pill(s) expelled, a timestamp of when the pill(s) was expelled, and so forth. In some embodiments, at least some of the electrical energy harvested during operation of the pill pack may be used to transmit one or more of the aforementioned data points to a remote computing device. In other embodiments, at least some of the electrical energy harvested during operation of the pill pack may be used to energize one or more LEDs.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be understood that certain expressions and reference signs used in the claims pursuant to Rule 6.2(b) of the Patent Cooperation Treaty ("PCT") do not limit the scope.

What is claimed is:

1. An energy harvesting apparatus, comprising:
    a housing, wherein the housing is configured to receive a pill pack; and characterized by:
    an energy harvesting electrical generator incorporated into the housing, wherein the electrical generator is adapted to convert motion associated with compression of at least one blister of the pill pack expelling one or more pills from the pill pack into electrical energy, wherein only at least some of the electrical energy resulting from such conversion of motion into electrical energy is used to collect one or more data points associated with operation of the pill pack during the expelling of the one or more pills; and
    an identification button, wherein the identification button is positioned so as to be activated when the one or more pills are expelled from the pill pack;
    wherein the one or more data points associated with the operation of the pill pack include an identification of the one or more pills expelled from the pill pack.

2. The energy-harvesting apparatus of claim 1, wherein the one or more data points comprise a timestamp.

3. The energy harvesting apparatus of claim 1, wherein the identification of the one or more pills expelled from the pill pack is determined based on a level of force required to expel the one or more pills.

4. The energy-harvesting apparatus of claim 1, further comprising a low power wireless transmitter integral with the housing, wherein at least some of the electrical energy is used to wirelessly transmit, from the low power wireless transmitter to a remote computing device one or more of data points.

5. The energy-harvesting apparatus of claim 4, wherein the low power wireless transmitter is a Bluetooth low energy transmitter, a ZigBee transceiver, or an EnOcean transceiver.

6. A method for harvesting and using electrical energy during compression of a pill pack positioned within a housing, comprising:
    operating the pill pack, wherein operating includes compressing at least one blister of the pill pack to expel at least one pill from the pill pack, and wherein operating further includes activating an identification button positioned so as to be activated when the one or more pills are expelled from the pill pack; and characterized by
    converting, by an energy harvesting electrical generator that is integral with the housing, motion associated with compression of the at least one blister into electrical energy; and
    using only at least some of the electrical energy resulting from such conversion of motion into electrical energy to collect one or more data points associated with operation of the pill pack during expulsion of the at least one pill, wherein the one or more data points include an identification of the at least one pill expelled from the pill pack.

7. The method of claim 6, wherein operating the pill pack further comprises identifying the one or more pills expelled from the pill pack.

8. The method of claim 6, wherein the electrical generator comprises a linear alternator.

9. The method of claim 6, wherein the one or more data points include a timestamp indicating a time that the at least one pill was expelled from the pill pack.

10. The method of claim 6, wherein the electrical generator comprises a piezoelectric strip.

11. The method of claim 6, further comprising utilizing at least some of the electrical energy to wirelessly transmit, from a low power wireless transmitter integral with the housing to a remote computing device, one or more of the data points.

12. The method of claim 11, wherein the low power wireless transmitter is a Bluetooth low energy transceiver or a ZigBee transceiver.

13. An energy harvesting apparatus, comprising:
    a housing, wherein the housing is configured to receive a pill pack; and
    an energy harvesting electrical generator incorporated into the housing, wherein the electrical generator is adapted to convert motion associated with compression of at least one blister of the pill pack expelling one or more pills from the pill pack into electrical energy, wherein only at least some of the electrical energy resulting from such conversion of motion into electrical energy is used to collect one or more data points associated with operation of the pill pack during the expelling of the one or more pills;
    wherein the one or more data points associated with the operation of the pill pack include an identification of the one or more pills expelled from the pill pack, and wherein the identification of the one or more pills expelled from the pill pack is determined based on a level of force required to expel the one or more pills.

* * * * *